(12) United States Patent
Frederick et al.

(10) Patent No.: US 10,201,314 B2
(45) Date of Patent: Feb. 12, 2019

(54) SYSTEM AND METHOD FOR EVALUATION OF CIRCULATORY FUNCTION

(71) Applicants: Blaise Frederick, Belmont, MA (US); Lia Maria Hocke, Medford, MA (US); Yunjie Tong, Medford, MA (US)

(72) Inventors: Blaise Frederick, Belmont, MA (US); Lia Maria Hocke, Medford, MA (US); Yunjie Tong, Medford, MA (US)

(73) Assignee: MCLEAN HOSPITAL CORPORATION, Belmont, MA (US)

( * ) Notice: Subject to any disclaimer, the term of this patent is extended or adjusted under 35 U.S.C. 154(b) by 633 days.

(21) Appl. No.: 14/389,400

(22) PCT Filed: Apr. 3, 2013

(86) PCT No.: PCT/US2013/035061
§ 371 (c)(1),
(2) Date: Sep. 30, 2014

(87) PCT Pub. No.: WO2013/152066
PCT Pub. Date: Oct. 10, 2013

(65) Prior Publication Data
US 2015/0065827 A1 Mar. 5, 2015

Related U.S. Application Data

(60) Provisional application No. 61/619,471, filed on Apr. 3, 2012.

(51) Int. Cl.
| | |
|---|---|
| A61B 5/1455 | (2006.01) |
| A61B 5/00 | (2006.01) |
| A61B 5/0205 | (2006.01) |
| A61B 5/021 | (2006.01) |

(Continued)

(52) U.S. Cl.
CPC ............ *A61B 5/7246* (2013.01); *A61B 5/021* (2013.01); *A61B 5/0205* (2013.01); *A61B 5/0261* (2013.01); *A61B 5/1455* (2013.01); *A61B 5/14546* (2013.01); *A61B 5/14551* (2013.01); *A61B 5/6826* (2013.01);
(Continued)

(58) Field of Classification Search
None
See application file for complete search history.

(56) References Cited

U.S. PATENT DOCUMENTS

| | | |
|---|---|---|
| 2010/0016731 A1 | 1/2010 | Eggers et al. |
| 2010/0191080 A1 | 7/2010 | Mills |

OTHER PUBLICATIONS

International Search Report and Written Opinion dated Jun. 24, 2013 in connection with PCT/US2013/035061.

*Primary Examiner* — Eric Winakur
*Assistant Examiner* — Marjan Fardanesh
(74) *Attorney, Agent, or Firm* — Quarles & Brady LLP

(57) ABSTRACT

A system and method for evaluating a circulatory function of an individual includes at least one connection configured to receive signals indicative of functional data relating to at least one functional parameter of the cardiovascular system of the subject and to at least two disparate locations on the subject. A processor is coupled to the at least, one connection and configured to receive the functional data from the at least one connection. The processor is also configured to compare the functional data to identify variations that deviate from an expected delay associated with the disparate locations and provide an assessment of the cardiovascular system function based on the comparison of the functional data.

27 Claims, 4 Drawing Sheets

(51) Int. Cl.
  *A61B 5/026*  (2006.01)
  *A61B 5/145*  (2006.01)
(52) U.S. Cl.
  CPC .......... *A61B 5/7253* (2013.01); *A61B 5/7282* (2013.01); *A61B 2562/04* (2013.01)

SYSTEM AND METHOD FOR EVALUATION OF CIRCULATORY FUNCTION

CROSS-REFERENCE TO RELATED APPLICATIONS

This application represents the national stage entry of PCT International Application No. PCT/US2013/035061 filed Apr. 3, 2013, which claims priority to U.S. Provisional Application Ser. No. 61/619,471, filed Apr. 3, 2012, both of which are hereby incorporated herein by reference for all purposes.

STATEMENT REGARDING FEDERALLY SPONSORED RESEARCH

This invention was made with Government support under Grant Number DA027877 awarded by the National Institutes of Health. The Government has certain rights in this invention.

BACKGROUND OF THE INVENTION

The present invention relates generally to systems and methods for the evaluation of a circulatory function and, more particularly, to systems and methods for analyzing propagation of blood stream attributes through a circulatory system to identify an attribute thereof and, thereby, acquire clinically useful information about a subject.

In an individual, a large number of conditions can result in poor operation of and blood flow through the circulatory system. Example conditions include, but are not limited to, vessel occlusion, loss of muscular tone, edema, arterial hardening, peripheral arterial disease, artherosclerosis, abnormal sympathetic or parasympathetic function, and cerebral or autonomic dysfunction.

In many cases, to diagnose these conditions by the analysis of blood flow through an individual, it is necessary to use expensive imaging equipment to detect and/or quantify an ineffective operation of the circulatory system, or highly trained personnel, or both. For example, imaging devices such magnetic resonance imaging (MRI) systems can be used, such as to perform so-called functional MRI (fMRI) procedures that rely on the as blood-oxygen-level-dependent (BOLD) contrast mechanism, to acquire indirect information about the flow of blood through a subject. As another example, an MRI system can be used in conjunction with an injected contrast agent that flows through and can be imaged within the vasculature to identify abnormal attributes of blood flow through an individual's circulatory system. Using these images, clinicians attempt to trace the abnormal attributes to a particular condition. Unfortunately, these imaging systems are expensive and complicated to operate making the diagnosis of a condition by these methods expensive and time consuming. Furthermore, in the case of so-called contrast enhanced MRI studies that rely on the injection of a gadolinium-based contrast agent, there are clinical indications and scientific evidence that the contrast agent, itself, can be extremely harmful to a sub-section of the population and, in the case of nephrogenic systemic fibrosis, deadly. Other methods include the use of injected radioactive tracer materials, which carry their own risks and expense. Other methods, such as ankle brachial index (ABI) measurements, require trained operators, and manipulations of blood flow with pressure cuffs which may be difficult or impossible in some patient groups, such as the obese.

These existing methods also are measurements at a single point of time, and in most cases require moving the subject to a procedure room. These methods cannot be used for continuous circulatory monitoring, or monitoring at home, for example.

Therefore, it would be desirable to have alternative or even complementary systems and methods for evaluating the performance of a subject's circulatory system, particularly, systems and methods that are more widely available and more cost effective than expensive imaging modalities, such as MRI and radionuclide methods, and is free of associated health risks, and systems that can measure circulation passively, continuously, and/or automatically.

SUMMARY OF THE INVENTION

The present invention overcomes the aforementioned drawbacks by providing systems and methods for evaluation of a circulatory function using readily-available and fairly-inexpensive technologies, such as optical imaging. More particularly, the present invention provides systems and methods for analyzing propagation of blood stream attributes to derive clinically useful information about the subject and the current operation of the subject's circulatory system.

In accordance with one aspect of the invention, a system is disclosed that is configured to analyze cardiovascular system function of a subject. The system includes at least one connection configured to receive signals indicative of functional data relating to at least one functional parameter of the cardiovascular system of the subject and to at least two disparate locations on the subject. The system also includes a processor coupled to the at least one connection and configured to receive the functional data from the at least one connection and compare the functional data to identify variations that deviate from an expected delay associated with the disparate locations. The processor is also configured to provide an assessment of the cardiovascular system function based on the comparison of the functional data.

In accordance with another aspect of the invention, a system configured to analyze cardiovascular system function of a subject is disclosed that includes at least two sensors located at disparate locations on the subject and configured to acquire functional data relating to at least one functional parameter of the cardiovascular system of the subject at the disparate locations. The system also includes a processor configured to receive the functional data from the at least two sensors and assemble the functional data into respective waveforms associated with respective disparate locations of the at least two sensors. The processor is further configured to compare the waveforms to identify variations between the waveforms that deviate from an expected delay associated with the disparate locations and provide an assessment of the cardiovascular system function based on the comparison of the waveforms.

In accordance with yet another aspect of the invention, a method for evaluating a circulatory function of an individual is disclosed that includes capturing a first dataset from a first sensor configured to detect blood flow fluctuations at a first location on the individual. A second dataset is captured from a second sensor configured to detect blood flow fluctuations at a second location on the individual. A temporal shift is determined between the first dataset and the second dataset and a report is generated, using the determined temporal shift that identifies a circulatory dysfunction in the individual.

The foregoing and other aspects of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
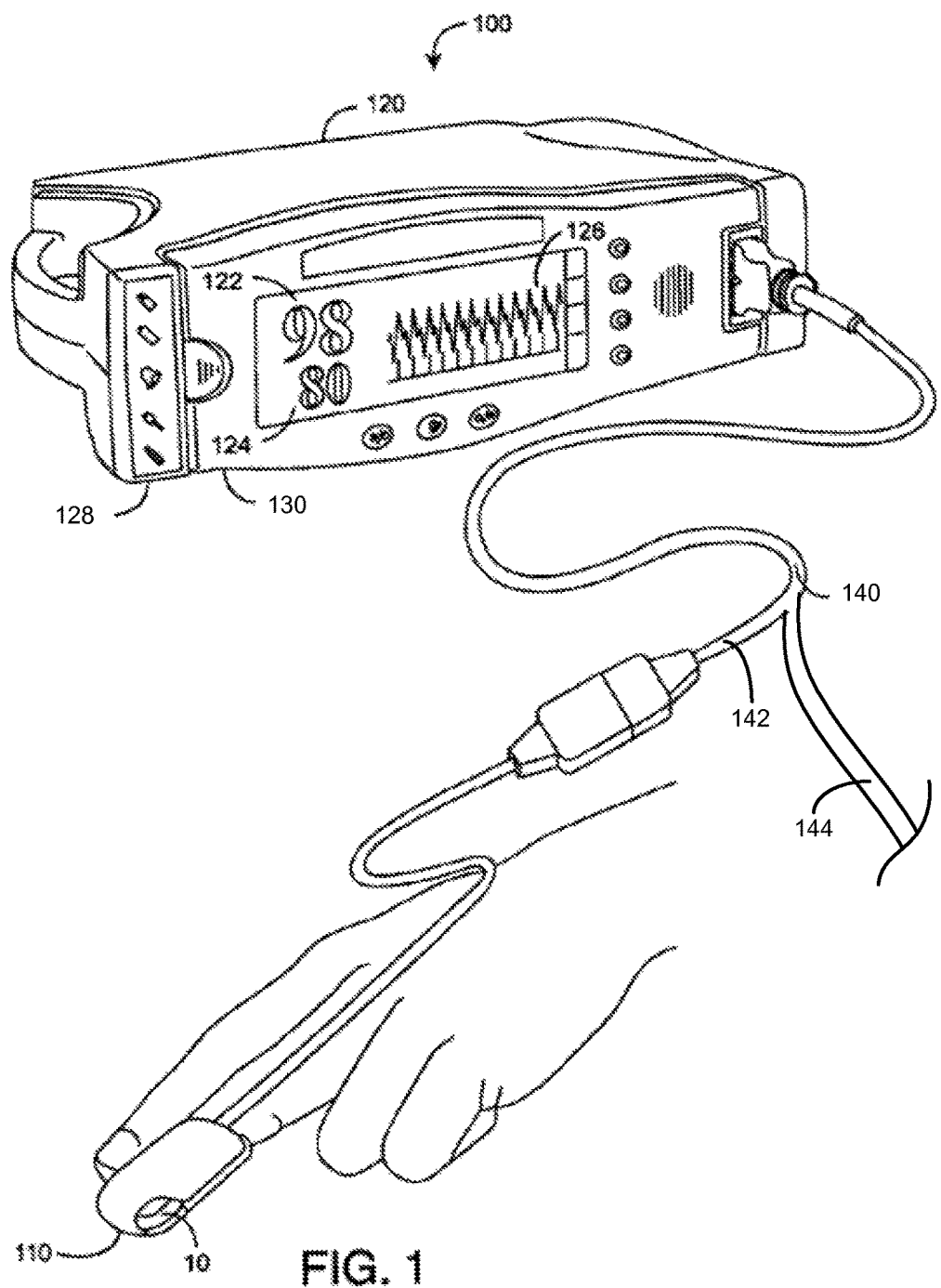
FIG. 1 is an illustration of a differential monitoring system in accordance with the present invention that, in the illustrated configuration, utilizes a pulse oximeter to monitor attributes of an individual's blood flow.

The present invention recognizes that, at a particular location in an individual's circulatory system, blood oxygenation and concentration levels naturally fluctuate on a variety of timescales. A first set of fluctuations, referred to as low-frequency oscillations (LFOs), oscillate in the range of approximately 0.01 Hertz (Hz) to 0.15 Hz. A second set of fluctuations, referred to as cardiac band fluctuations, oscillate in the range of approximately 0.7 Hz to 3 Hz. A third set of fluctuations, referred to as respiratory fluctuations, oscillate in the range of approximately 0.2 Hz to 0.67 Hz.

It has been determined that these fluctuations are carried or communicated through the blood stream as the blood circulates throughout the individual's body. The fluctuations are carried both in the blood itself, as well as in pressure waves that travel through the blood. Deficiencies in the individual's circulatory system can cause the arrival time of these various fluctuations at different locations of the body to vary or otherwise deviate from an expected tolerance. These endogenous fluctuations in oxygenation and concentration levels can be detected at different locations as they travel via the individual's blood stream. By comparing signals acquired from different locations of the body, the relative strength and propagation delay of the blood and the pressure waves associated with the fluctuations can be compared.

The present invention further recognizes that the detected propagation delays and signal strengths carry information about the condition of the blood stream supplying each location and, furthermore, this information can be used to determine characteristics of the blood vessels and the blood content of the individual. Consequently, the present invention recognizes that a comparison of the signals detected at different locations of the body can be used to provide diagnostic information about circulatory function and/or pathology in the individual.

One technique for monitoring particular characteristics of blood flowing within the body is near-infrared spectroscopy (NIRS). NIRS is a method of spectroscopy that exploits the absorptivity of certain substances in the near-infrared region to identify the contents of materials, such as blood. NIRS can be used to identify the contents (e.g., blood sugar levels) of blood, as well as blood-oxygen characteristics and changes in blood volume. In these conventional uses of NIRS, highly-localized information, such as provided by a NIRS monitor located on an individual's finger, is gathered and characteristics of the blood flowing through that highly-localized area is determined, such as the blood sugar or oxygenation of blood in that finger. However, as will be described, the present invention recognizes that NIRS and other monitoring mechanisms and systems can be used to monitor fluctuations in oxygenation and concentration, as well as other properties, in the blood stream at a local level, but also to couple such measurements into non-local and even global systems. For example, when configured into differential diagnosis systems, the present invention includes analysis systems and methods so that data can be generated regarding wide-scale circulatory function and dysfunction.

For example, referring to FIG. 1, pulse oximeters are devices that use NIRS to monitor characteristics of an individual's circulation. FIG. 1, for example, shows a system using a pulse oximeter to monitor attributes of an individual. As shown in FIG. 1, a system 100 includes a sensor 110, a monitor 120, and a cable 140 connecting the sensor 110 and the monitor 120. In accordance with the present invention, the cable 140 may include multiple branches 142 and 144. In this regard, the illustrated sensor 110 is connected to one location on the individual, such as the fingertip 10. Though omitted from FIG. 1 for simplicity, a sensor similar to that of the illustrated sensor 110 is located at a terminal end of branch 144 to monitor another fingertip, such as located on the individual's right hand, or any of a wide variety of other locations on the individual, such as the foot, neck, and the like.

Figure 2:
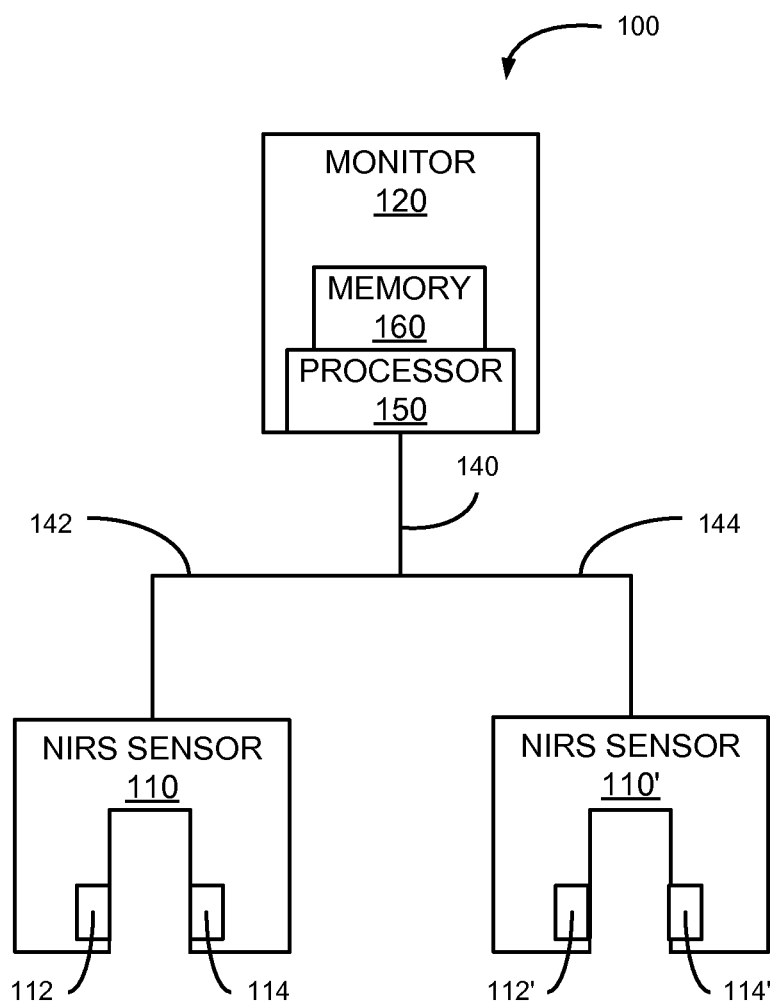
FIG. 2 is a schematic diagram showing functional components of the present system for evaluating the circulatory function of an individual.

Referring to FIGS. 1 and 2, the sensors 110 and 110' may have optical emitters 112 and 112' and detectors 114 and 114' and each attached to an individual at a selected fleshy medium site, such as a fingertip 10, as shown, or a toe or an ear lobe. For example, the sensors 110 and 110' may be continuous blood pressure monitoring sensors or other sensors, such as will be described. The emitters 112 and 112' are positioned to project light of through the blood vessels and capillaries of the fleshy medium. The detectors 114 and 114' are positioned to detect the emitted light after absorption and scattering by the fleshy medium, including hemoglobin and other constituents of pulsatile blood flowing within the fleshy medium, and generate signals corresponding to the intensity of the emitted light.

For example, each sensor 110 and 110' may be configured to measure the transmission and/or reflectance of one or more wavelengths of light in the red or near infrared spectrum (e.g., of wavelengths from approximately 650 nanometers (nm) to 1100 nm) in a tissue sample. The sensors 110 and 110' may, for example, illuminate tissue with one or more wavelengths of light and record the light incident on one or more photodetectors that capture light emitted from that tissue.

The sensors 110 and 110' can illuminate the tissue in a continuous or time varying fashion, depending on the particular design of the sensor or probe. The time variation in tissue reflectance and/or transmission can be measurable at the frequency or frequencies of interest. Example frequencies of interest include the LFO band, the cardiac band, the respiratory band, and combinations thereof. The captured signals can be processed further (for example, by monitor 120) or may be recorded for later analysis.

The monitor 120, which may be a standalone device or may be incorporated as a module or built-in portion of a multiparameter monitoring system, computes at least one physiological parameter responsive to the signals acquired by the sensors 110 and 110', such as magnitudes of detected intensity signals. The monitor 120 can provide a numerical readout of the individual's oxygen saturation 122, a numerical readout of pulse rate 124, and a display of the patient's plethysmograph 126, which provides a visual display of the patient's pulse contour and pulse rate, and other parameters, for example, such as the relative strength of signals in various bands, such as the cardiac and LFO bands.

In the system of the present invention, a processor 150 is provided, which by way only of example may be included in the monitor 120. Also, a memory 160 may be coupled to the processor 150. The memory 160 stores instructions that cause the processor to execute methods, such as will be described in greater detail below.

The signals captured from any of the sensors 110 and 110' can be used directly by the processor 150, or may transformed using various formulae before performing further analysis. The sensors 110 and 110' are configured to measure fluctuations in local hemodynamic parameters in various frequency ranges and the processor 150 may be programmed to determine a variety of time-varying characteristics or metrics. A portion of the hemodynamic signal detected by the sensors 110 and 110' at various locations on the individual's body results from the global oxygenation and concentration signal passing through the sensitive region of the sensor's optical probe. The processor 150 can determine the degree of global signal shared between the sensors 110 and 110' using a cross-correlation function. The maximum amplitude of the correlation function indicates the degree of shared signal, and the time lag of the maximum amplitude of the correlation function indicates the difference in arrival time of the signals at the location of the two sensor 110 and 110', and whether one signal lags or leads the other.

In accordance with the present invention, by comparing the times at which each sensor 110 and 110' detects particular fluctuations in the individual's blood flow, the processor 150 is able to characterize attributes of the individual's circulatory system, such as time delays or correlation strengths, thereby providing clinical information to aid in diagnosing a condition resulting in circulatory dysfunction.

The calculated time delays and/or correlation strengths in one or more frequency bands between one or more sensors, or the changes in those measured during or between exams, or relative to predetermined values, can be presented numerically or graphically on a display provided by the monitor 120 or other display system, and/or analyzed automatically and compared to expected values, and/or recorded for later analysis.

For example, the above-described system may be used as a diagnostic system for assessing peripheral arterial blockage and for monitoring patients during/after peripheral angioplasty or peripheral bypass surgery.

Figure 3:
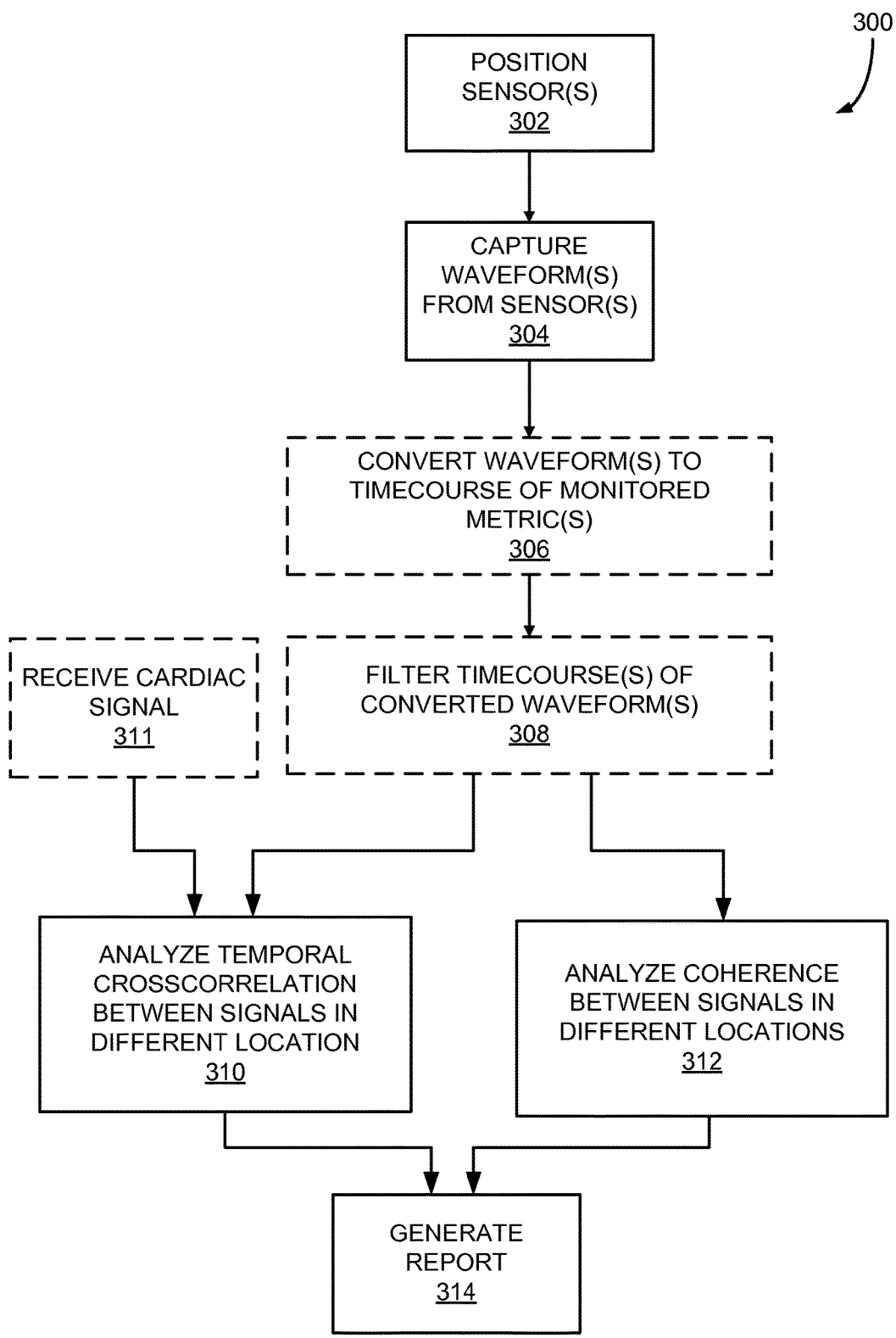
FIG. 3 is a flowchart setting forth exemplary steps of a method for analyzing data from a differential monitoring system positioned on an individual to identify a circulatory dysfunction.

Referring to FIG. 3, a flowchart is provided illustrating a method 300 for analyzing waveforms captured from two or more sensors positioned on an individual to identify a circulatory dysfunction. In step 302, two or more sensors, such as NIRS sensors, are positioned on the individual's body, generally at disparate locations, such as fingers of opposing hands or the like. When using a sensor pair, the sensors may be positioned on the individual's fingers and toes, or fingers on both hands, or toes on different feet, or different locations on the head, or between a location on the head and on a finger or toe, or a finger and over a major muscle, for example. That is, the sensors do not need to be on different limbs or regions, but should positioned to monitor regions supplied by different portions of the vasculature. For example, if trying to diagnose a circulatory dysfunction in a single finger, two adjacent fingers can be monitored. Fingers and toes are provided as examples because they are convenient locations for sensor and have very different vascular sources. As such, they can be advantageous for certain clinical applications, such as diagnosing circulatory problems in diabetes, because positions far from the heart at the end of long arterial paths provide clean indications of such problems. However, if the duration for recording data is not of consequence, even extremely close sensors can provide suitable differential data.

In step 304, after the sensors are positioned, data is collected, for example, in the form of time-varying waveforms. For example, in the case of NIRS sensors the data may be representative of multi-wavelength red/near-infrared spectroscopic waveforms, for example, including two wavelengths of approximately 690 nm and 830 nm. These or other wavelengths may be selected to differentiate a characteristic of blood, such as differentiation of oxy and deoxy hemoglobin within the individual's bloodstream. In other implementations, only a single infrared wavelength (for example, of approximately 830 nm) is captured if there is no requirement to consider species separately, but additional wavelengths generally provide additional independent measures resulting in an improved signal to noise ratio (SNR) in the captured data. By increasing the SNR, shorter measurement times, and improved differentiation of oxy and deoxy hemoglobin can be achieved, so that the identification of different types of circulatory dysfunction may be facilitated.

After the waveforms are captured, in step 306 the waveforms are converted to a timecourse of monitored metrics. For example, raw optical measurements may be converted to measurements of the changes in oxy and deoxy hemoglobin, for example, using a Modified Beer-Lambert law transform. By way of the transform or associated processing the captured signals may be used to derive estimates of the variation in concentration of oxyhemoglobin and/or deoxyhemoglobin, and/or total hemoglobin, or some other parameter that reflects temporal changes in blood parameters. In one implementation of the present system, oxyhemoglobin and total hemoglobin waveforms are derived for analysis. The Modified Beer-Lambert law transform is mentioned here because it is well known and computationally inexpensive. Other transforms can be used, or no transform at all. If multidistance optical measurements are made at each recording site, more sophisticated processing can be used to calculate absolute (rather than relative) oxy- and deoxyhemoglobin concentration waveforms, which would provide additional diagnostic information. In other implementations of the system, though, no transformation is necessary. In that case, the captured raw waveforms can be analyzed directly to observe temporal variation in the captured signals using the raw optical signal. The temporal variation can then be used to identify circulatory dysfunction, as described below. However, by performing the transformation of step 306, or other transforms, it may be possible to improve the SNR in the captured data using covarying to remove some irrelevant measurement factors.

In optional step 308, the timecourse of monitored metrics may be filtered into a number of relevant frequency bands. In one implementation, for example, the timecourses are filtered into the LFO band and the cardiac band. These bands are variably defined in literature, but the LFO band generally occurs between approximately 0.01 Hz and 0.15 Hz. The cardiac band, which captures the heartbeat waveform and a few harmonics, so the shape will not be overly distorted, generally occurs between approximately 0.7 Hz and 4.0 Hz.

It has been observed that portions of the time variation of the oxy and deoxy hemoglobin concentrations propagate through the bloodstream at two dominant speeds—the speed of bulk average blood flow, and the speed of wave propagation through the blood. Generally, the LFO signal travels at the speed of average bulk flow, while the cardiac signal travels at the wave propagation speed. As a result, there will be variable timeshifts between the LFO signal and the cardiac signal in different measurement sites throughout the body. By quantifying the amount of global signal in each frequency band at each location, and the relative timeshifts between locations (and between frequency bands), it is possible to infer properties of the circulatory system.

The present method may use either of at least two alternative methods to analyze the captured signals to determine properties of the circulatory system.

In step 310, the system can use the temporal cross-correlation between a pair of LFO signals or pair of cardiac signals generated at different locations on the individual to determine a degree of similarity between the signals as a function of delay time. A cross-correlation function provides a method of estimating the similarity of two signals and the time delay between those signals. The time delay between the signals can be averaged over time or calculated over multiple (perhaps overlapping) time periods to capture dynamic variation in hemodynamics, either at rest, or in response to some action on the part of the subject or some intervention (e.g. changing body orientation, performing a mental or physical action, changing breathing pattern, occlusion of a blood vessel, and the like).

The correlation function in different frequency bands can be used to identify a number of blood propagation parameters. For example, because the LFO signal appears to primarily move with the blood itself, the LFO signal allows estimation of the relative arrival times of blood at different regions of the body by examining the cross-correlation of the LFO signals at the locations of the sensors. The cardiac fluctuation signal, however, travels as a pressure wave through the vasculature, moving faster than the blood carrying the fluctuation. As a result, a dedicated cardiac signal, such as from an electrocardiogram (EEG) may, optionally, be acquired at step 311. Regardless of whether separately acquired or derived from the optical data, the cross-correlation of the cardiac signals may be derived to yield further information about the differences in pressure wave propagation speed.

The delay time may correspond to the temporal shift between points of maximum similarity (i.e., highest correlation coefficient) between the two locations. The amplitude of the correlation coefficient at that time delay indicates the degree of shared signal between the locations. The shape of the peak (e.g., the width and asymmetry) can also be analyzed to determine attributes of the individual's blood vessels nearby the sensor locations. Broader peaks, for example, may indicate increased drag in the vessels leading to one or the other sensor location.

Delay times between different sensor pairs may indicate pathology. For example, preliminary data acquired in healthy subjects indicates that the LFO signal in the left big toe lags the signal in the left index finger by 2.5-4 seconds. A delay time significantly longer than this may indicate impaired circulation to the left leg, which may be a result of a chronic condition such as arterial blockage or circulatory problems associated with diabetes. Similarly, if the delay is greater than 0.5-1 second between two sensors placed on fingers of opposite hands, that may indicate thoracic outlet syndrome.

Additionally or alternatively, in step 312, the system may calculate the coherence of a pair of signals captured from the sensors. The coherence carries the same types of information as the cross-correlation, described above, but in the spectral domain. Accordingly, a similar analysis may be made of the coherence of the two signals to determine temporal shift between sensor locations that, as described above, are indicative of an attribute of the individual's blood vessel.

In step 312, it is not necessary to split the captured data into bands before comparing the two signals as the similarity between signals is indicated as a function of frequency, and the phase value at each frequency location gives and indication of time delay.

Other techniques for filtering the data captured from the sensors include using time domain or Fourier domain band-pass filter (e.g., 0.01 Hz<LFO<0.15 Hz). The two derived LFO signals can then be cross-correlated in order to calculate the maximum correlation and corresponding temporal shifts between these two signals.

When implementing the above-described method 300, the relative blood arrival times of different fluctuations are determined at different locations on an individual. It should be noted that this approach is not simply calculating propagation delays between two locations on the individual. Because all blood going to the individual's periphery comes from the left ventricle through the aorta, that is the probable source region for the blood flow. Accordingly, the time differences detected represent the difference in arrival time from the aorta to the tissue of interest. Given the aorta's depth, it is difficult to make a pure NIRS measurement of the signal in the aorta from outside the body, though in some circumstances this may be possible using a catheter or an endoscopic probe. In some implementations, as described above, for example with respect to step 311, the heartbeat signal could be detected using an electrocardiography (EKG) system to determine absolute wave propagation time.

Taking these considerations of the disparate locations of the sensors and the implications of general heart function with respect to the disparate locations, the process ends at step 314 with the generation of a report on the cardiovascular function of the subject being monitored. For example, the generated report may simply be a waveform, such as could be communicated via a display on the monitor 120 of FIG. 1. Other reports may include detailed written or printed reports, auditory or visual alerts and the like.

The present system may be implemented as a set of NIRS probes clipped to a finger on each hand of an individual, a toe on each foot, one toe and one finger, and one or more locations on the scalp to record signals simultaneously. The captured signals can then be compared. This technique or equipment would provide a relatively inexpensive method for measuring circulatory dysfunction that may be caused by, for example, inadequate or compromised perfusion of peripheral or other tissue either chronically, for example due to diabetes or obstructive artery disease, or acutely as the result of an injury or intervention; abnormalities in relative blood arrival time, which may signal arterial blockage, venous prolapse, or other circulatory problems such as stroke or carotid occlusion. Further, differential blood arrival times may be affected by abnormal vascularization, such as in tumors or arteriovenous malformations or shunts.

Figure 4:
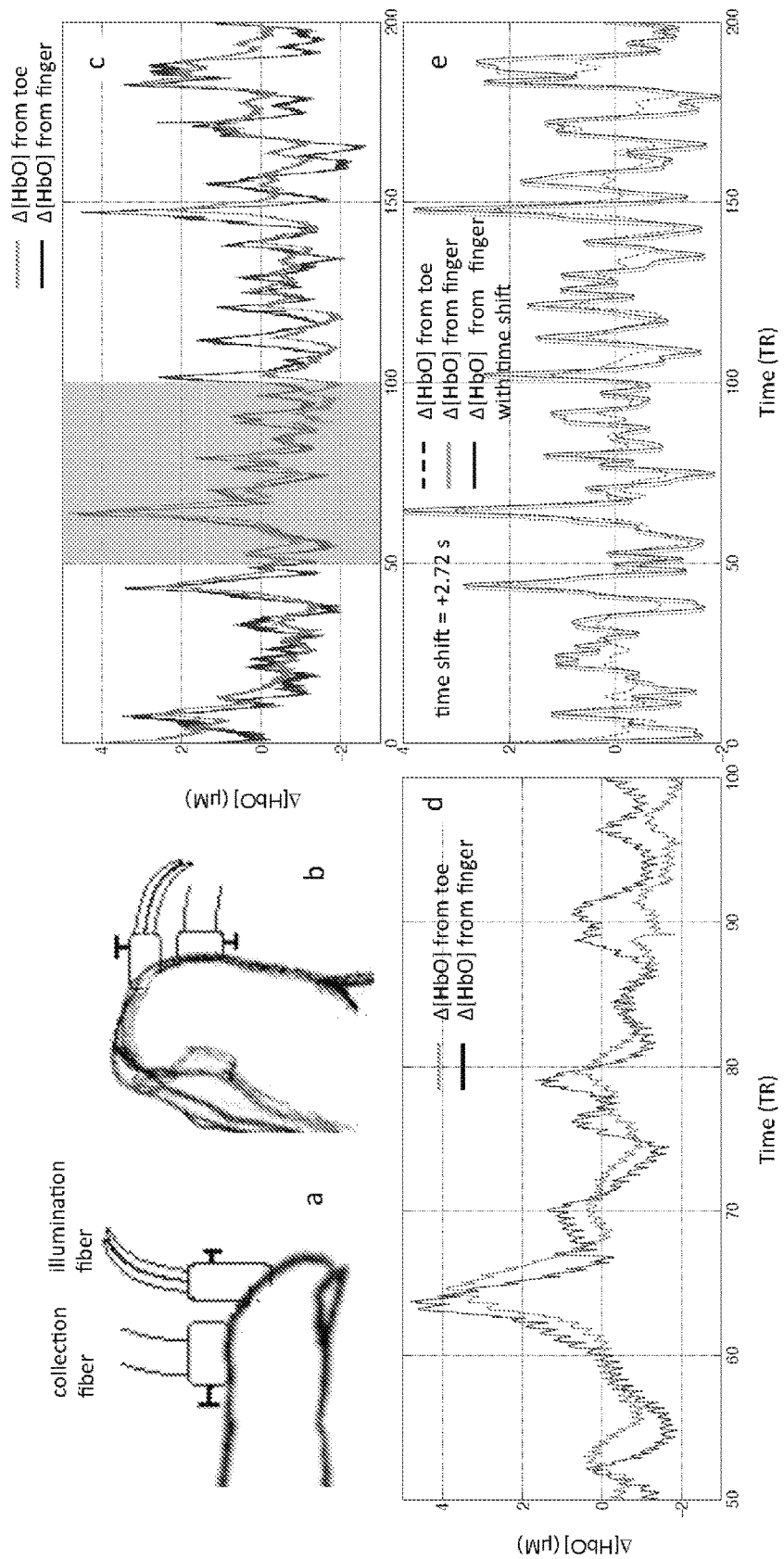
FIGS. 4A-E illustrate an exemplary sensor configuration and associated reports generated with the exemplary sensor configuration.

For example, referring now to FIGS. 4A and 4B, an exemplary system is illustrated with the exemplary placement of the NIRS probes on the middle fingertip (FIG. 4A) and the big toe (FIG. 4B). FIG. 4C illustrates one exemplary report of temporal traces of Δ[HbO] obtained by the NIRS at the fingertip and left toe. FIG. 4D illustrates an enlarged section of FIG. 4C (indicated by gray block). The LFO signal of the finger and toe from, elucidate that the signal measured at the toe is 2.72 s later than that of the finger, as best illustrated in FIG. 4E. Time is given in TR (repetition time in fMRI).

Alternatively, the system can use one or more NIRS source detector pairs located some distance apart, where one or more of the detectors are inserted into one or more blood vessels with a catheter. Differential timing of the signals detected by the NIRS sensors can be used to measure blood velocity and propagation directly.

In some implementations of the device, one or more of the NIRS probes can use multiple source-detector distances at a location to provide absolute measurement of hemoglobin concentrations.

Some of the functional units described in this specification have been described as modules in order to more particularly emphasize their implementation. For example, a "module" including the monitor, processor, and memory was described. However, a module may be implemented in a hardware circuit or may be separated or distributed. Modules may also be implemented in software for execution by various types of processors. An identified module of executable code may, for example, comprise one or more physical or logical blocks of computer instructions which may, for example, be organized as an object, procedure, or function. Nevertheless, the executables of an identified module need not be physically located together, but may comprise disparate instructions stored in different locations which, when joined logically together, comprise the module and achieve the stated purpose for the module.

The schematic flow chart diagrams included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Where, "data storage media," or "computer readable media" is used, Applicants mean an information storage medium in combination with the hardware, firmware, and/or software, needed to write information to, and read information from, that information storage medium.

The present invention has been described in terms of one or more preferred embodiments, and it should be appreciated that many equivalents, alternatives, variations, and modifications, aside from those expressly stated, are possible and within the scope of the invention.

The invention claimed is:

1. A system configured to analyze cardiovascular system function of a subject, the system comprising:
    at least one connection configured to receive signals indicative of data relating to at least one parameter of the cardiovascular system of the subject and to at least two disparate locations on the subject;
    a processor coupled to the at least one connection and configured to:
        receive the data from the at least one connection;
        transform the data into timecourses of monitored metrics associated with respective the disparate locations;
        filter the timecourses into a predetermined number of frequency bands, wherein at least one of the frequency bands includes frequencies corresponding to a low frequency oscillations (LFO) band;
        analyze the timecourses after filtering to identify variations that deviate from an expected delay associated with the disparate locations; and
        generate an assessment report of the cardiovascular system function based on the analysis of the timecourses after filtering.

2. The system of claim 1 further comprising at least two sensors configured to derive the data from the subject and connected to the at least one connection to communicate the signals.

3. The system of claim 1 wherein the processor is further configured to determine, from the data, at least one of endogenous fluctuations in oxygenation and concentration levels at the disparate locations.

4. The system of claim 3 wherein the processor is further configured to determine a relative strength and propagation delay of at least one of blood flow and the pressure waves associated with the endogenous fluctuations.

5. The system of claim 1 wherein the processor is further configured to perform a Modified Beer-Lambert law transform to the data.

6. The system of claim 1 wherein at least one of the frequency bands includes frequencies corresponding to a cardiac band.

7. The system of claim 1 further comprising at least one sensor connected to the at least one connection and in communication with the processor, the processor configured to differentiate oxy and deoxy hemoglobin within the cardiovascular system.

8. The system of claim 1 wherein the processor is configured to determine at least one of a speed of bulk average blood flow and a speed of wave propagation through blood within the cardiovascular system from the data to identify variations that deviate from the expected delay associated with the disparate locations.

9. The system of claim 1 wherein the processor is further configured to determine a phase value at each of a plurality of frequencies in the data to determine a time delay between the data and indicate the time delay to provide the assessment of the cardiovascular system function.

10. A system configured to analyze cardiovascular system function of a subject, the system comprising:
   at least two sensors located at disparate locations on the subject and configured to acquire data relating to at least one parameter of the cardiovascular system of the subject at the disparate locations;
   a processor configured to:
      receive the data from the at least two sensors;
      assemble the data into respective waveforms associated with respective disparate locations of the at least two sensors;
      transform the data into timecourses of monitored metrics associated with respective the disparate locations;
      filter the timecourses into a predetermined number of frequency bands, wherein at least one of the frequency bands includes frequencies corresponding to a low frequency oscillations (LFO) band;
      analyze the timecourses after filtering to identify variations between the waveforms that deviate from an expected delay associated with the disparate locations; and
      generate an assessment report of the cardiovascular system function based on the analysis of the timecourses after filtering.

11. The system of claim 10 wherein the processor is further configured to transform the data into respective timecourses of monitored metrics associated with respective ones of the at least two sensors and the associated disparate locations.

12. The system of claim 11 wherein the processor is further configured to perform a Modified Beer-Lambert law transform to the data.

13. The system of claim 10 wherein at least one of the frequency bands includes frequencies corresponding to a cardiac band.

14. The system of claim 10 wherein the at least two sensors are in communication with the processor, the processor configured to differentiate oxy and deoxy hemoglobin within the cardiovascular system.

15. The system of claim 14 wherein the processor is further configured to estimate a variation in concentration of at least one of oxy hemoglobin, deoxy hemoglobin, and total hemoglobin to determine temporal changes in blood parameters.

16. The system of claim 10 wherein the data includes temporal changes in blood parameters.

17. The system of claim 10 wherein the processor is configured to determine at least one of a speed of bulk average blood flow and a speed of wave propagation through blood within the cardiovascular system from the data to identify variations between the waveforms that deviate from an expected delay associated with the disparate locations.

18. The system of claim 10 wherein the processor is further configured to determine a temporal crosscorrelation between the waveforms taking into consideration the disparate locations of the at least two sensor to determine a degree of similarity between the waveforms as a function of delay time and indicate the similarity between the waveforms as the function of delay time to provide the assessment of the cardiovascular system function.

19. The system of claim 10 wherein the processor is further configured to determine a phase value at each of a plurality of frequencies in the waveforms to determine a time delay between the waveforms and indicate the time delay to provide the assessment of the cardiovascular system function.

20. The system of claim 10 wherein the at least two sensors include near-infrared spectroscopy (NIRS) sensors.

21. The system of claim 10 wherein the disparate locations include fingers of opposing hands.

22. A method for evaluating a circulatory function of an individual, comprising:
   capturing, at a first location on the individual, a first dataset from a first sensor configured to detect blood flow fluctuations at frequencies corresponding to low frequency oscillations (LFO);
   capturing, at a second location on the individual, a second dataset from a second sensor configured to detect blood flow fluctuations at frequencies corresponding to LFO;
   determining a temporal shift between the first dataset and the second dataset; and
   generating a report, using the determined temporal shift, identifying a circulatory dysfunction in the individual.

23. The method of claim 22 wherein the blood flow fluctuations include cardiac band fluctuations.

24. The method of claim 22 wherein the first sensor is a near-infrared spectroscopy (NIRS) and the second sensor is an NIRS sensor.

25. The method of claim 22 including transforming the first and second dataset using a modified Beer-Lambert law.

26. The method of claim 25 including converting timecourses of the first and second transformed datasets into frequency bands, wherein at least one of the frequency bands includes frequencies corresponding to the LFO.

27. The method of claim 22 wherein determining the temporal shift includes at least one of:
   i) determining a temporal crosscorrelation between the first dataset and the second dataset to determine a degree of similarity between the first dataset and the second dataset; and
   ii) determining a phase value at each of a plurality of frequencies in the first dataset and the second dataset to determine a time delay between the first dataset and the second dataset.

* * * * *